(12) United States Patent
Negre et al.

(10) Patent No.: US 9,072,865 B2
(45) Date of Patent: Jul. 7, 2015

(54) METHOD OF REGULATING CSF DRAINAGE

(75) Inventors: Philippe Negre, Paris (FR); Christophe Moureaux, Besancon (FR); Christophe Boyer, Miserey Salines (FR); Olivier Bonnal, Melsungel (DE)

(73) Assignee: SOPHYSA, Orsay (FR)

( * ) Notice: Subject to any disclaimer, the term of this patent is extended or adjusted under 35 U.S.C. 154(b) by 481 days.

(21) Appl. No.: 12/921,501

(22) PCT Filed: Mar. 13, 2009
(Under 37 CFR 1.47)

(86) PCT No.: PCT/IB2009/051054
§ 371 (c)(1),
(2), (4) Date: Jul. 26, 2011

(87) PCT Pub. No.: WO2009/113037
PCT Pub. Date: Sep. 17, 2009

(65) Prior Publication Data
US 2011/0275976 A1 Nov. 10, 2011

(30) Foreign Application Priority Data
Mar. 14, 2008 (FR) ...................... 08 51684

(51) Int. Cl.
*A61M 27/00* (2006.01)
*G01F 1/68* (2006.01)
(52) U.S. Cl.
CPC ..... *A61M 27/006* (2013.01); *A61M 2205/3379* (2013.01); *G01F 1/68* (2013.01)
(58) Field of Classification Search
CPC .................. A61M 1/00; A61M 27/00
USPC .......................................... 604/8–10
See application file for complete search history.

(56) References Cited

U.S. PATENT DOCUMENTS

| 4,776,838 | A  | * | 10/1988 | Sainte-Rose et al. ............. 604/9 |
| 6,926,691 | B2 | * | 8/2005  | Miethke ........................... 604/9 |
| 7,011,095 | B2 | * | 3/2006  | Wolf et al. ..................... 128/898 |
| 2002/0052563 | A1 |   | 5/2002  | Penn et al. |

(Continued)

FOREIGN PATENT DOCUMENTS

| DE | 196 54 990 A1 | 6/1998 |
| EP | 0 156 974 A2 | 10/1985 |

(Continued)

OTHER PUBLICATIONS

International Search Report mailed May 20, 2009 issued International Patent Application No. PCT/IB2009/051054.

(Continued)

*Primary Examiner* — Melanie Hand
(74) *Attorney, Agent, or Firm* — Oliff PLC

(57) ABSTRACT

An implantable drainage device for draining the cerebrospinal fluid of a patient, the device including:
a drainage valve including a valve member and a valve seat;
a control unit suitable for modifying an operating parameter of said valve, at least as a function of a measurement (D) of the fluid flow rate through said valve;
an actuator controlled by the control unit, suitable for modifying the operation of said valve as a function of said operating parameter as modified by the control unit; and
a mass flowmeter suitable for evaluating said flow rate of fluid through said valve.

20 Claims, 4 Drawing Sheets

(56) References Cited

U.S. PATENT DOCUMENTS

| | | |
|---|---|---|
| 2004/0068201 A1* | 4/2004 | Saul .............................. 600/561 |
| 2005/0038371 A1* | 2/2005 | Reich et al. ....................... 604/9 |
| 2005/0171452 A1 | 8/2005 | Neff |
| 2006/0000273 A1 | 1/2006 | Keppner et al. |
| 2006/0001550 A1* | 1/2006 | Mann et al. .............. 340/870.07 |

FOREIGN PATENT DOCUMENTS

| | | |
|---|---|---|
| EP | 1 612 523 A3 | 1/2006 |
| JP | A-5-19422 | 7/1985 |
| JP | A-2002-524198 | 8/2002 |
| JP | A-2004-513681 | 5/2004 |
| JP | A-2006-17723 | 1/2006 |
| WO | WO 00/15149 A1 | 3/2000 |
| WO | WO 02/07596 A1 | 1/2002 |
| WO | WO 2006/115724 A1 | 11/2006 |
| WO | WO 2009/113037 A1 | 9/2009 |

OTHER PUBLICATIONS

Written Opinion of the International Searching Authority mailed May 20, 2009 issued International Patea Application No. PCT/IB2009/051054.

Notice of Reasons for Rejection dated Apr. 16, 2013 from Japanese Patent Application No. 2010-550323 (with English-language translation).

* cited by examiner

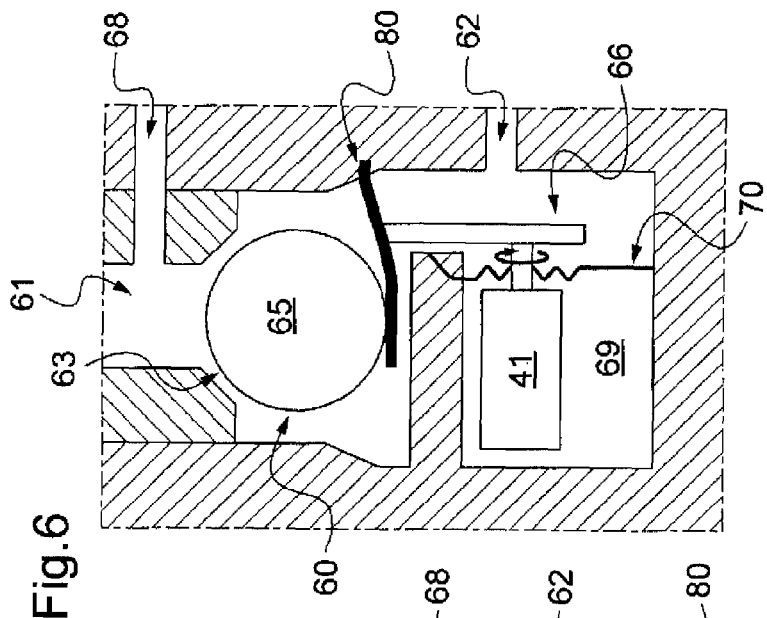
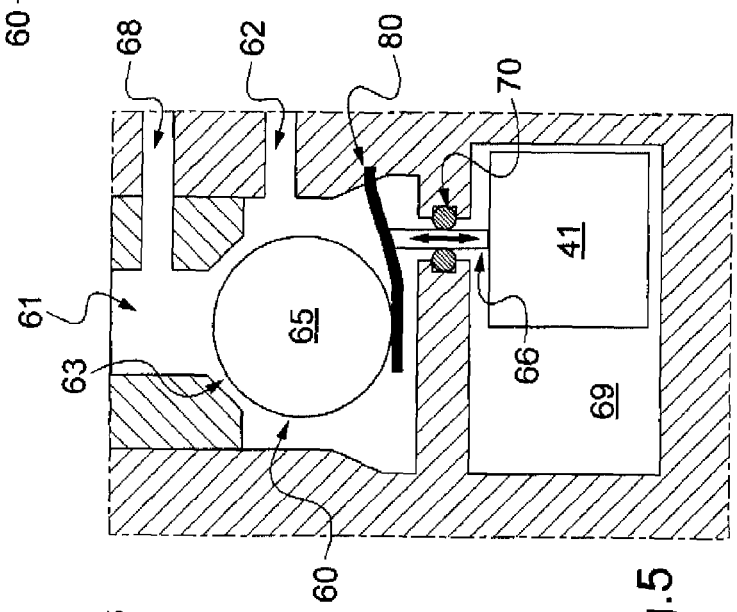
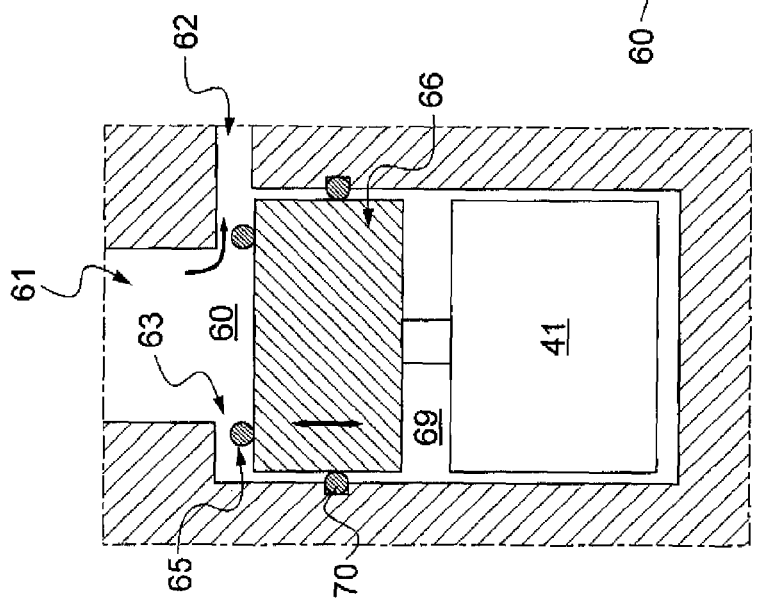

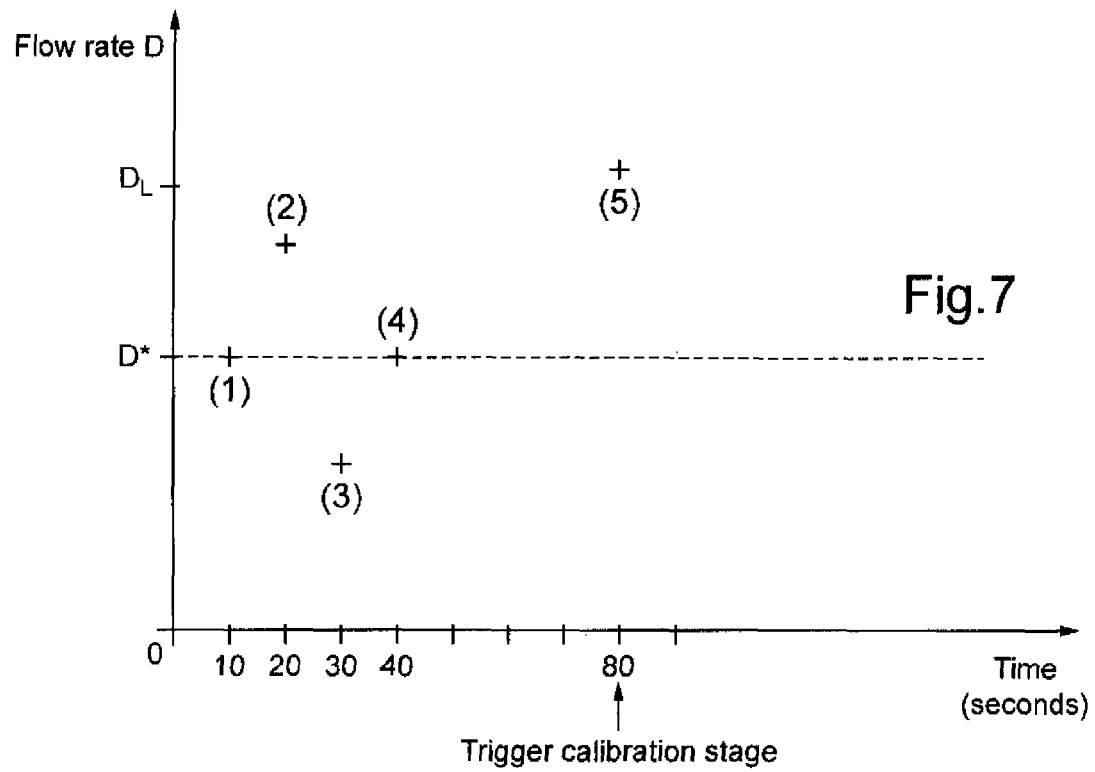
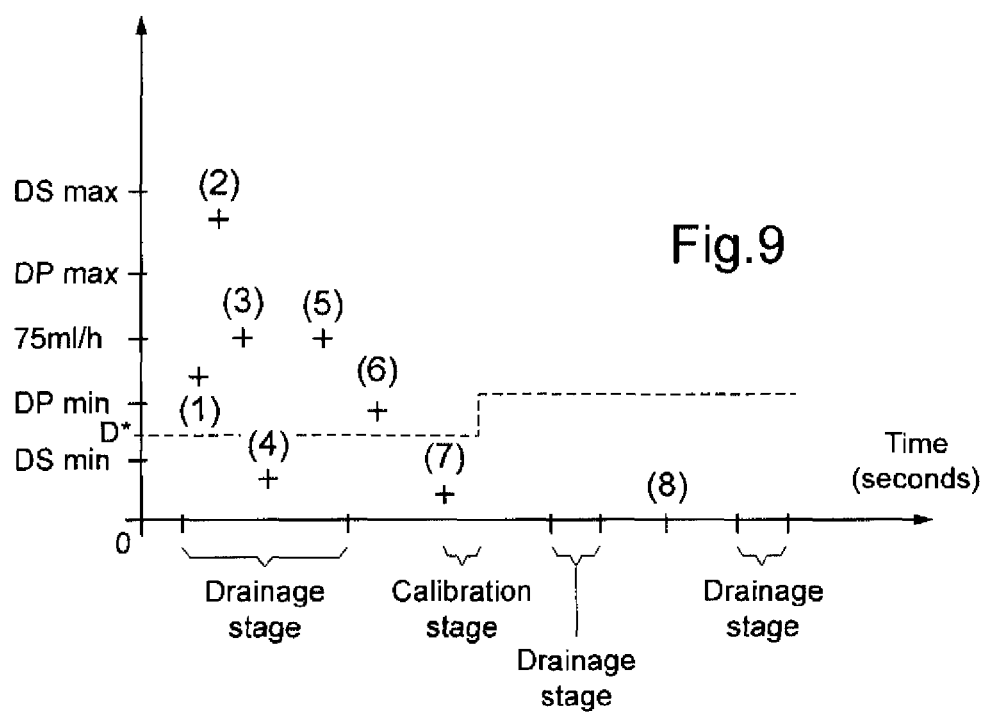

METHOD OF REGULATING CSF DRAINAGE

The invention relates to an implantable drainage device for draining the cerebro-spinal fluid (CSF) of a patient, and it also relates to methods of implementing the device. Such a device is intended in particular for treating hydrocephalus. It serves to shunt the cerebro-spinal fluid contained in the ventricles in the cranial cavity to some other site for resorption, e.g. the peritoneal cavity.

BACKGROUND OF THE INVENTION

Conventionally, a drainage device comprises a drainage valve presenting operation that is modifiable as a function of a measured pressure difference, as described in DE 196 54 990. The pressure difference must then be measured between the inlet and the outlet of a very narrow passage of small diameter, thereby specifically running a major risk of the passage becoming obstructed. Furthermore, a pressure difference sensor generally presents problems of stability and of drift over time.

Also, international application WO 2006/115724 discloses an implantable mass flowmeter suitable for transmitting a signal to the outside of a patient, which signal is representative of a cerebro-spinal fluid flow rate. The flow rate measurement can thus be communicated to a third party. Nevertheless, that flowmeter is not used in association with a device that enables the opening conditions of a drainage valve to be modified.

A particular object of the present invention is to provide an implantable drainage device that does not present the above-mentioned drawbacks.

SUMMARY OF THE INVENTION

The present invention thus provides an implantable drainage device for draining the cerebro-spinal fluid of a patient, the device comprising: a drainage valve comprising a valve member and a valve seat; a control unit suitable for modifying an operating parameter of said valve, at least as a function of a measurement of the fluid flow rate through said valve; and an actuator controlled by the control unit, suitable for modifying the operation of said valve as a function of said operating parameter as modified by the control unit.

By way of example, with an on/off valve, the control unit may be suitable for modifying the value of the bolus duration, i.e. the length of time the valve remains open, as a function of a measurement of the flow rate of cerebro-spinal fluid through the valve, and the actuator may be suitable for modifying the operation of the valve as a function of the value of the bolus duration as modified by the control unit.

The drainage device of the present invention is remarkable in that it further comprises a mass flowmeter suitable for evaluating said flow rate of fluid through said valve.

As described in greater detail in the description below, the implantable drainage device according to exemplary embodiments of the invention advantageously enables cerebro-spinal fluid to be drained effectively and reliably, is capable of being adapted easily, or even automatically, to the needs of the patient, and to the patient's living conditions.

DETAILED DESCRIPTION OF THE INVENTION

Mass Flowmeter

The term "mass flowmeter" is used to designate a Coriolis effect flowmeter or a thermal flowmeter, i.e. a meter providing measurements of the flow rate of a fluid that depends on the thermal capacity of the fluid. A mass flowmeter therefore needs to be rated as a function of the nature of the fluid for which it is desired to measure the flow rate. Conventionally, the operating principle of a mass flowmeter relies on evaluating heat exchange between the fluid and its environment while the fluid flows between an upstream point and a downstream point. By way of example, the evaluation may result from measuring the power required for maintaining a constant temperature difference between those two points, or conversely from measuring the temperature at the downstream point while the temperature at the upstream point is kept constant. In order to evaluate the flow rate, the mass flowmeter therefore has no need to make use of the pressure difference $P_d$ from upstream to downstream of the drainage valve.

The mass flowmeter is preferably a thermal flowmeter, in particular including means for using the principle of thermodilution to keep a temperature difference constant between an upstream point and a downstream point through which at least a fraction of the cerebro-spinal fluid passes in succession. The flowmeter also includes means for measuring the power needed to keep said difference constant, and means for evaluating the flow rate of the cerebro-spinal fluid through the valve on the basis of said power measurement.

It is possible to use a mass flowmeter using a measurement principle similar to that of the LIQUI-FLOW® series sold by the supplier BRONKHORST.

In a variant, the mass flowmeter may alternatively be a thermal flowmeter having temperature sensors suitable for measuring upstream and downstream temperatures at upstream and downstream points through which the cerebro-spinal fluid passes in succession. It also includes means for heating said fluid at a point situated between the upstream and downstream points, using a determined power level, and means for evaluating the flow rate of the cerebro-spinal fluid on the basis of the upstream and downstream temperatures and of said power level.

It is also possible to use a flowmeter of the kind described in international application WO 2006/115724 and adapted to be able to communicate with the implanted control unit.

The flowmeter may take measurements D of the flow rate of the cerebro-spinal fluid on a permanent or an intermittent basis, in particular solely during a drainage stage, i.e. a stage during which a given volume of cerebro-spinal fluid is being evaluated. By way of example, the frequency with which measurements are taken may be no more than once every 10 seconds, every 20 seconds, every hour, or every day, or indeed every week.

This makes it possible to limit the energy consumption of the flowmeter.

Preferably, the frequency with which flow rate is measured by the flowmeter varies as a function of the circadian rhythm and/or the position of the patient, e.g. prone or standing, and/or as a function of predetermined time periods, e.g. while cerebro-spinal fluid is being drained.

Also preferably, the frequency increases or decreases as a function of the flow rate measured for the cerebro-spinal fluid. In particular, if the measured flow rate remains stable, then the frequency may be decreased.

Drainage Valve and Operating Parameters

The drainage valve used in the implantable drainage device according to exemplary embodiments of the invention may be of three different types: a "passive" valve with programmable pressure; a "progressive" valve; or preferably, an "on/off" valve.

A passive valve comprises:
an internal chamber;

at least one inlet port and at least one outlet port communicating with the internal chamber;

a valve member;

a valve seat associated with the inlet port or the outlet port, the valve member being capable of bearing against said seat in order to isolate the inlet port from the outlet port; and resilient return means urging the valve member to bear against the seat, and arranged to exert an opening pressure $P_0$ on the valve member.

The actuator may be configured so as to be capable of modifying the opening pressure $P_0$.

Under such circumstances, an "operating parameter" is the opening pressure $P_0$ of the drainage valve.

The resilient return means may be constituted in particular by a helical or flat spring or by a diaphragm tending to urge the valve member against the valve seat.

A progressive valve comprises:

an internal chamber;

at least one inlet port and at least one outlet port communicating with the internal chamber;

a valve member;

a valve seat associated with the inlet port or the outlet port, the valve member being capable of bearing against said seat in order to isolate the inlet port from the outlet port;

the actuator being configured to be capable of modifying the position of the valve member relative to the valve seat, i.e. the degree of opening $\Delta_0$ of the valve, between an extreme open position and an extreme closed position, and thus of allowing a flow to pass through the seat at a variable rate.

Under such circumstances, "operating parameters" are the degree of opening $\Delta_0$ of the valve and the duration $t_\Delta$ that a position is maintained with the degree of opening $\Delta_0$.

An on/off valve, such as that described in U.S. Pat. No. 6,926,691, comprises:

an internal chamber;

at least one inlet port and at least one outlet port communicating with the internal chamber;

a valve member;

a valve seat associated with the inlet port or the outlet port, the valve member being capable of bearing against said seat in order to isolate the inlet port from the outlet port;

the actuator being configured so as to be capable of modifying the position of the valve member relative to the valve seat between an extreme open position and an extreme closed position, with the intermediate positions being necessarily transient.

Under such circumstances, "operating parameters" are the frequency $F_0$ at which the valve is opened and the duration during which the valve remains open, referred to as the "bolus duration" and written $t_b$.

Depending on the type of valve, the operating parameter may thus be the opening pressure $P_0$, or the degree of opening $\Delta_0$, or the opening frequency $F_0$, or indeed the duration $t_\Delta$ or the bolus duration $t_b$.

Adjusting the operating parameter serves in particular to modify the rate at which cerebro-spinal fluid is evacuated through the drainage valve, and as a result to modify the volume of cerebro-spinal fluid that is evacuated through the drainage valve.

This adjustment preferably enables the operation of the implantable drainage device to be adapted, in particular so that the rate at which cerebro-spinal fluid is evacuated through the valve corresponds to a setpoint flow rate D* for the cerebro-spinal fluid to be evacuated.

When the drainage valve is an on/off valve or a progressive valve, the actuator may also act on the valve member via resilient return safety means, in particular a helical or flat spring, or a diaphragm. The tension of the resilient return safety means is preferably modifiable.

The return force exerted by the resilient return safety means on the valve member is determined so as to cause a "safety opening" to take place, i.e. to cause the valve to move in the opening direction, in the event of the pressure difference $P_d$ from upstream to downstream of the valve exceeding a determined safe pressure $P_s$, e.g. greater than or equal to 250 millimeters of water (mmH$_2$O), e.g. equal to 300 mmH$_2$O or 400 mmH$_2$O.

Preferably, the implantable drainage device according to exemplary embodiments of the invention has means for detecting the safe pressure $P_s$ being exceeded. These means may for example comprise the flowmeter, means for measuring the power consumed by the actuator, a position sensor for sensing the position of the resilient return safety means, or means for measuring pressure upstream and/or downstream of the valve, e.g. a pressure sensor.

The implantable drainage device then includes means for modifying an operating parameter ($\Delta_0$, $F_0$, $t_\Delta$, $t_b$) accordingly.

The device may include pressure measurement means for measuring pressure upstream and/or downstream of the valve, for performing functions other than detecting the security pressure $P_s$ being exceeded, e.g. for evaluating the pressure difference $P_d$ from upstream to downstream of the valve, in particular for evaluating whether a cleaning operation is needed.

Control Unit and Actuator

The control unit may include a regulator suitable for controlling the actuator, in particular by adjusting one or more operating parameters so that the measured flow rate is servo-controlled to the setpoint flow rate D*.

The control unit may also be suitable for modifying the operation of the drainage valve when the flow rate measurement D moves outside an "optimum accuracy range" (defined below as the range [$DP_{min}$ to $DP_{max}$]) of the flowmeter in which accuracy is maximized, i.e. in which measurement error is minimized, and/or a "safe range" (defined below as the range [$DS_{min}$ to $DS_{max}$]) outside which there exists some particular risk for the patient.

In particular, the control unit may be configured in such a manner as to keep the measured value D of the flow rate of cerebro-spinal fluid through the valve greater than a predetermined lower limit $DP_{min}$, preferably greater than 50 milliliters per hour (mL/h), more preferably greater than 60 mL/h, and/or less than a predetermined upper limit $DP_{max}$, preferably less than 100 mL/h, more preferably less than 80 mL/h.

The control unit may also be configured in such a manner as to keep the measured value D of the flow rate of cerebro-spinal fluid through the valve remains greater than a predetermined minimum safe flow rate $DS_{min}$, which rate may be zero, and/or less than a predetermined maximum safe flow rate $DS_{max}$.

Thus, when the flowmeter measures a cerebro-spinal fluid flow rate that is greater than $DP_{max}$ and/or $DS_{max}$, or less than $DP_{min}$ and/or $DS_{min}$, the control unit may act on the actuator, e.g. via the regulator, so that the measured value D of the cerebro-spinal fluid flow rate is brought back towards a predetermined value, e.g. of 75 mL/h.

This type of control serves in particular to avoid excessively increasing the flow rate of cerebro-spinal fluid, in particular in the event of the patient changing position or during periods of paradoxical sleep.

The actuator may include an electric motor that is self-blocking in the event of its electrical power supply being interrupted, so as to enable the valve member to be held in position without consuming power.

The electric motor is preferably a motor of the piezoelectric type or the electrostatic type. Advantageously, such a motor is insensitive to disturbances associated with magnetic fields. The electric motor may also be an induction motor.

The actuator may also include a piezoelectric spring blade.

Preferably, the drainage device includes means for keeping the valve in the closed position. Such means are used in particular for testing the behavior of the patient, and in particular for verifying shunt independence.

Setpoint Flow Rate D*

The setpoint flow rate D* for the cerebro-spinal fluid to be evacuated may be determined by a doctor, or even by the control unit, for example.

The setpoint flow rate D* may be determined in particular as a function of:

- a value representative of the mean flow rate and/or of the total volume as measured over a determined duration, e.g. greater than one hour, greater than one day, or greater than one week, for example; and/or
- the mean value of the pressure difference $P_d$ from upstream to downstream of the valve, when the patient is in the standing position or in the sitting position, and on average over a determined period, e.g. one week; and/or
- the time of day, with it being possible in particular for the setpoint flow rate D* to be greater at night than in the daytime.

Typically, the setpoint flow rate D* is increased or decreased in the event of hypodrainage or hyperdrainage, respectively.

In addition, at regular intervals or following a need being detected, the setpoint flow rate D* may be set manually or by the control unit to a value that is less than or equal to the value corresponding to the real production of cerebro-spinal fluid by the patient's body.

External Communication Means

The implantable drainage device according to exemplary embodiments of the invention may also include communication means for communicating externally from the patient's body.

The communication means may comprise a receiver suitable for receiving control instructions transmitted from outside the patient's body, e.g. setpoints and/or programming codes and/or power, in particular for activating the actuator and/or powering the control unit and/or powering the mass flowmeter.

The communication means may also comprise a transmitter suitable for transmitting information to the exterior of the patient's body, which information relates to the device, e.g. an identity code, a history of various applied setpoint values, and/or relates to the state of the patient, and/or a history of values for the volume or the flow rate of the cerebro-spinal fluid that has been drained during a given period.

Furthermore, the communication means, in particular the transmitter and/or the receiver, may implement a radio frequency link.

By way of example, the implantable drainage device according to exemplary embodiments of the invention may include a radio antenna made up of circular turns.

The control unit may include memory means for storing information received or transmitted by the receiver and/or the transmitter and/or a communications unit external to the patient's body.

In a variant, the memory means are situated in a memory unit that is different from the control unit, and that is included in the device according to exemplary embodiments of the invention.

The device according to exemplary embodiments of the invention may include a power supply, in particular a power supply suitable for powering the control unit and/or the actuator and/or the flowmeter, e.g. an optionally rechargeable battery and/or a thermoelectric generator.

Intermittent Drainage Mode

In a first particular embodiment of the invention, making use of "intermittent" drainage, the cerebro-spinal fluid is drained discontinuously, i.e. intermittently, during determined periods of time referred to as "drainage stages", or "bolus".

Under such circumstances, the drainage valve may be an on/off valve.

The flowmeter and/or the control unit and/or the actuator may be powered solely during drainage stages, preferably once every 10 seconds, more preferably once every 20 seconds.

In a variant, the actuator may be powered solely while the drainage valve is being opened or closed, i.e. respectively at the beginning and at the end of the drainage stage.

The flowmeter and/or the control unit and/or the actuator may also be powered other than during drainage stages, for example once every second, once every 5 minutes, or indeed 10 seconds after the end of the drainage stage, in particular for the purpose of detecting an unexpected flow of cerebro-spinal fluid through the valve, e.g. a non-zero flow, and of adapting the operation of the valve accordingly.

Powering the flowmeter and/or the control unit and/or the actuator intermittently, and in particular solely during drainage stages, serves in particular to greatly reduce energy consumption.

Without a Regulator

In the absence of a regulator, the control unit may operate at a determined frequency $F_0$ to perform drainage stages of a predetermined duration, referred to as the bolus duration $t_b$, so that the mean fluid evacuation rate is close to the setpoint rate D*.

By way of example, drainage stages may take place every 15 minutes, or every 30 minutes, or they may be separated by time intervals that are longer.

By way of example, the bolus duration $t_b$ may be determined by a doctor and may lie in the range 1 second to 15 minutes, or even more, for example.

Nevertheless, the frequency and/or the bolus duration may be modified temporarily, in particular as a function of the circadian rhythm of the patient.

In another possible embodiment, the control unit performs drainage stages at a determined frequency $F_0$, which stages are adapted to evacuate a predetermined bolus volume $V_b$ of cerebro-spinal fluid. The bolus duration is then variable.

For this purpose, during a drainage stage, the flowmeter may measure the flow rate of the cerebro-spinal fluid regularly, and the control unit may respond to said measurement by determining the volume V of cerebro-spinal fluid that has been evacuated through the valve since the beginning of the drainage stage.

When the evacuated volume V of cerebro-spinal fluid corresponds to the bolus volume $V_b$, the control unit acts on the actuator so as to close the drainage valve. The drainage stage is then terminated.

By way of example, if two drainage stages are performed within a single hour using a bolus volume $V_b$ of 10 millimeters (mL), the total volume of cerebro-spinal fluid that has been evacuated at the end of one hour will be 20 mL.

The bolus volume $V_b$ and the opening frequency $F_0$ may be determined, e.g. by a doctor, so as to be equal respectively to 10 mL and to one drainage stage every 15 minutes, 30 minutes, or more, for example.

On the basis of the bolus volume $V_b$, the control unit may determine the operating parameter $t_b$ as a function of flowmeter measurements taken during the drainage stage.

With a Regulator

In the presence of a regulator, in order to servo-control the mean evacuated flow rate on the setpoint flow rate $D^*$, the regulator may act on the drainage stage frequency $F_0$ or on the bolus duration $t_b$, either directly or by modifying the bolus volume $V_b$, as described above.

Regulation may be performed in particular in the manner described below.

At regular time intervals, e.g. between each of the drainage stages, or regularly after a determined number of drainage stages, or indeed after a determined period of time, e.g. once every hour, or every 6, 12, or 24 hours, the regulator performs a monitoring stage.

During the monitoring stage, it compares the mean flow rate (total volume of cerebro-spinal fluid that has been evacuated since the previous monitoring stage divided by $\Delta t$, where $\Delta t$ represents the time between two monitoring stages), and compares it with the setpoint flow rate $D^*$. The regulator then adjusts the opening frequency $F_0$ and/or the bolus duration $t_b$ so as to reduce any difference between the setpoint flow rate $D^*$ and the mean flow rate evacuated up to the following monitoring stage.

Permanent Drainage Mode

In a second particular embodiment of the invention, said to be using "permanent" drainage, the cerebro-spinal fluid is drained continuously, i.e. permanently.

Under such circumstances, the drainage valve may be a passive valve, or preferably a progressive valve.

A setpoint flow rate $D^*$ for the cerebro-spinal fluid that is to be evacuated is determined, e.g. by a doctor, e.g. to be equal to 20 mL/h.

Preferably, the setpoint flow rate $D^*$ is determined so as to lie within the "optimum accuracy range" and/or within the "safe range", as defined above.

With a passive valve, the opening pressure $P_0$ may be determined in such a manner that a mean flow rate of the cerebro-spinal fluid is substantially equal to $D^*$.

With a progressive valve, the degree of opening $\Delta_0$ may be modified by the actuator, e.g. as a function of the pressure of the cerebro-spinal fluid, so that the mean flow rate of cerebro-spinal fluid that is evacuated is substantially equal to $D^*$.

When the device includes a regulator, e.g. of the proportional (P), proportional integral (PI), or proportional integral differential (PID) type, the measured value D of the flow rate of cerebro-spinal fluid through the valve is compared with the setpoint flow rate D by the control unit. The regulator servo-controls the actuator by acting on $P_0$ or $\Delta_0$ so that the measured value D of the flow rate tends towards the setpoint flow rate value $D^*$.

Calibration Stage

Whatever the intended drainage mode, the control unit may be configured so as to trigger so-called "calibration stages" e.g. at regular intervals, preferably once every hour, more preferably once every day, still more preferably once every month, thereby enabling the setpoint flow rate $D^*$ to be corrected.

The control unit preferably includes a processor suitable, during calibration stages, for determining or modifying the setpoint flow rate $D^*$ for the cerebro-spinal fluid.

During calibration stages, the setpoint flow rate $D^*$ is re-evaluated, at least as a function of the measured value D of the cerebro-spinal fluid flow rate as delivered by the flowmeter.

In particular, the control unit may be suitable for re-evaluating the setpoint flow rate $D^*$ at regular intervals, in particular once every hour and/or immediately after the device has been implanted in the patient's body, and/or following a particular event, in particular in the event of an abnormal flow rate being detected.

Preferably, a calibration stage is always engaged after the drainage device according to exemplary embodiments of the invention has been implanted in the patient's body.

A calibration stage may also be triggered when the measured cerebro-spinal fluid flow rate D is found to be unexpected, i.e. abnormally high or abnormally low or not zero, possibly corresponding to the safe pressure $P_s$ being exceeded, or to a measured value D of the flow rate lying outside the safe and/or optimum accuracy range, or indeed to a malfunction of the implantable drainage device.

In general, the purpose of the calibration stages is to adapt the setpoint flow rate $D^*$ to the real rate at which the patient produces of cerebro-spinal fluid.

The setpoint flow rate $D^*$ is initially determined without knowing accurately the mean rate at which the brain produces cerebro-spinal fluid.

In addition, the rate at which cerebro-spinal fluid is produced may vary over a patient's lifetime, thereby requiring the setpoint flow rate $D^*$ to be adapted correspondingly.

For example, it may be that the setpoint flow rate $D^*$ is under-estimated relative to the mean rate at which cerebro-spinal fluid is produced by the brain.

Under such circumstances, the intracranial pressure of the patient will increase abnormally and the differential pressure $P_d$ will likewise increase abnormally.

An abnormal increase in differential pressure $P_d$ may give rise in particular to an abnormal flow rate being detected, e.g. over a duration that is abnormally long and/or at a moment that is unexpected. For example it may give rise to the safe flow rate $DS_{max}$ being exceeded or to a limit flow rate $D_L$ being exceeded, or to the safe pressure $P_s$ being exceeded, e.g. equal to 300 mmH$_2$O or 400 mmH$_2$O.

The limit flow rate $D_L$ may be equal to, or preferably less than, the safe flow rate $DS_{max}$, so as to detect an abnormal flow rate before reaching a pressure difference $P_d$ that is potentially harmful for the safety of the patient.

The setpoint flow rate $D^*$ is thus modified and increased accordingly by the control unit, e.g. by 1 mL/h.

More particularly with the intermittent drainage mode, an abnormal increase in pressure difference $P_d$ gives rise to safety opening of the valve. By way of example, this safety opening may be detected by measuring a non-zero flow rate D of cerebro-spinal fluid between two drainage stages.

The value of the setpoint flow rate $D^*$ is then increased, e.g. by 1 mL/h, with this continuing so long as a non-zero measured value D of cerebro-spinal fluid flow rate is detected between drainage stages.

A doctor may also attempt progressively to improve the natural drainage capacities of the patient.

The doctor may thus decide to set the setpoint flow rate $D^*$ at a lower value, e.g. a value that is 2 mL/h less than the value strictly necessary for compensating the mean production of cerebro-spinal fluid.

In a variant, the control unit may take the place of the doctor in setting the setpoint flow rate $D^*$ in this way.

The patient's organism may thus progressively recover its own physiological functions of evacuating cerebro-spinal fluid.

Cleaning Stage

The control unit may also be configured to initiate a "cleaning stage" at regular intervals, e.g. at least once a week or once a month or at the request of a person, in particular a doctor, or indeed following the detection of an abnormal flow rate, e.g. a non-zero flow rate at a time when the drainage valve ought to be closed.

A cleaning stage may also be triggered when the pressure difference $P_d$ or a mean pressure difference $P_d$ over a predetermined duration exceeds a predetermined threshold value.

The control unit then acts on the actuator in such a manner as to cause the valve member to be spaced apart from its seat by a spacing of at least 0.5 millimeters (mm), preferably of at least 0.8 mm, more preferably of at least 1 mm, for a duration of at least 5 seconds, and preferably of at least 10 seconds.

Cleaning stages serve in particular to clear particles such as debris or organic deposits that might obstruct the valve defined by the drainage valve seat.

The control unit may also be configured so as to close the drainage valve completely in the event of the flowmeter detecting a reversal in the flow direction of the cerebro-spinal fluid through the drainage valve, in particular in the event of a measured value D of the cerebro-spinal fluid flow rate that has a negative sign.

Drainage System

The invention also relates to a drainage system comprising a device according to exemplary embodiments of the invention, the device having communication means for communicating with the exterior of the patient's body, and a non-implantable control unit, suitable for communicating, in particular by radio, with said communication means after said device has been implanted.

By way of example, the control unit may enable information to be recovered relating to the identity of the valve, to a history of different setpoint values that have been applied, in particular the different values for the setpoint flow rate D*, it may transmit power to the drainage device, it may trigger cleaning stages, and/or it may trigger calibration stages.

Method

The invention also provides a method of controlling a valve of a drainage device for draining the cerebro-spinal fluid of a patient, in particular a device according to exemplary embodiments of the invention, the method comprising regulation on the basis of a setpoint flow rate D* that is defined to have a value that is lower than the value needed for exactly compensating the production of cerebro-spinal fluid by the patient, e.g. a value that is 2 mL/h lower.

It can thus be expected that the patient's organism will progressively recover its own physiological evacuation functions.

DESCRIPTION OF THE FIGURES

Other characteristics and advantages of the invention appear further from the description of the drawings, given for non-limiting descriptive purposes. In the drawings:

FIGS. 2, 3, 4, 5, and 6 are cross-sections through examples of drainage valves suitable for use in a device according to exemplary embodiments of the invention;

FIG. 7 is a graph showing an example of how the measured flow rate D varies as a function of time in an embodiment with permanent drainage;

FIG. 9 is a graph showing an example of how the measured value D of the flow rate varies as a function of time in an embodiment using intermittent drainage;

In the various embodiments, references are selected to be identical when designating members that are identical or analogous.

In order to facilitate understanding the various figures, dimensions are not necessarily to scale.

DETAILED DESCRIPTION OF PREFERRED EMBODIMENTS OF THE INVENTION

Figure 1:
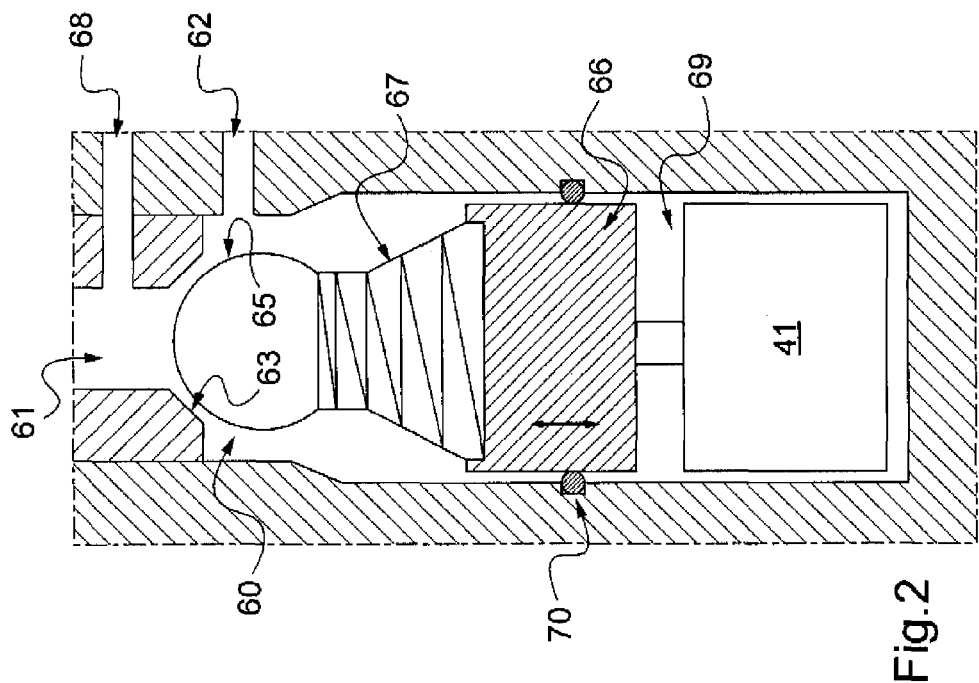
FIG. 1 is a diagram of a device according to exemplary embodiments of the invention.

FIG. 1 shows an implantable drainage device 10 made in accordance with the invention, and implanted in the body 20 of a patient.

The device comprises a control unit 40, an actuator 41, a drainage valve 42, a mass flowmeter 43 having temperature sensors $T_2$ and $T_1$, a power supply 44, and a transceiver 45.

The flow direction of the cerebro-spinal fluid is represented by arrow F.

The control unit 40 receives power from the power supply 44 and/or from the transceiver 45 that can also serve to transmit control instructions to the control unit 40. It also receives information relating to the flow rate of the cerebro-spinal fluid as measured by the flowmeter 43.

The control unit 40 then controls the actuator 41 that acts on the drainage valve 42, e.g. by modifying the position of the valve member relative to the valve seat.

By way of example, the power supply 44 is an optionally rechargeable battery and/or a thermoelectric generator that is electrically connected to the control unit 40.

The transceiver 45, e.g. a radio antenna having circular turns serves to communicate with a control unit 50 outside the patient's body 20, e.g. a transceiver for sending and receiving information and power at radio frequency.

The control unit 40 may optionally include the transceiver 45.

The implantable drainage device 10 may optionally have no power supply 44, in particular when the transceiver 45 is capable of supplying sufficient power to the control unit 40 from outside the patient's body 20 to enable the actuator 40 to be activated.

The mass flowmeter 43 measures the flow rate of the cerebro-spinal fluid flowing through the valve 42, by means of two temperature sensors $T_2$ and $T_1$, and the measured value D for the flow rate is delivered to the control unit 40.

The temperature measurements taken by the temperature sensors $T_2$ and $T_1$ are compared with each other so as to determine the temperature difference that exists between the two temperature sensors $T_2$ and $T_1$, this temperature difference being proportional to the flow rate of the cerebro-spinal fluid.

The control unit 40 may determine an operating parameter ($P_0$, $\Delta_0$, $F_0$, $t_A$, $t_b$) from the measured flow rate D.

The operating parameter can then enable the actuator 41 to modify the operation of the drainage valve 42.

Figure 2:
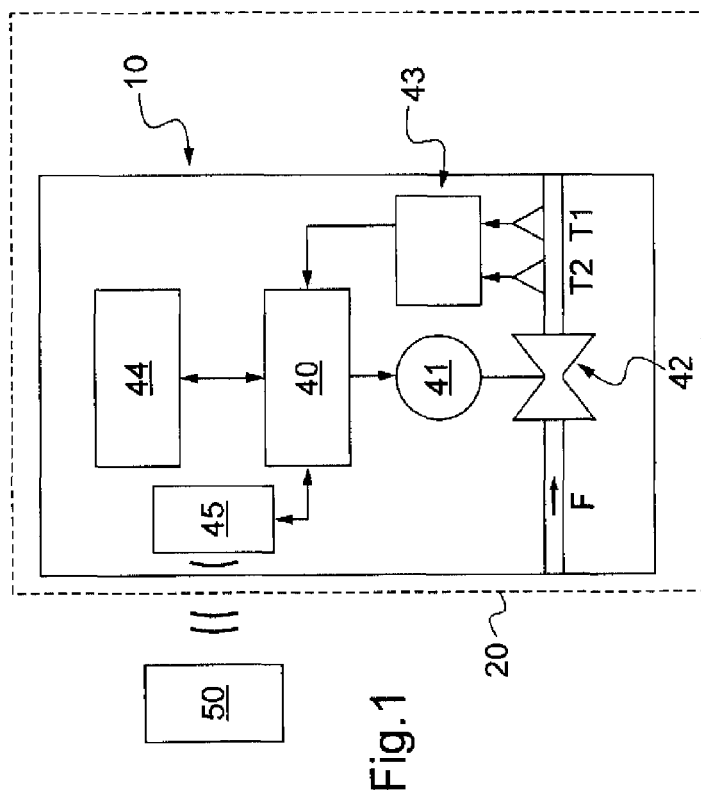

FIG. 2 shows a preferred example of the type of drainage valve 42 that is suitable for use in the device 10.

The drainage valve 42 has an internal chamber 60, inlet and outlet ports 61 and 62, a valve seat 63, a valve member 65 in the form of a ball, and a pusher 66. The pusher 66 is mechanically coupled to the actuator that is in the form of a motor 41, and it acts on the ball 65 via a helical spring 67 so as to urge the ball towards the valve seat 63.

The drainage valve 42 may also include a second inlet port 68 serving, for example, to enable a plurality of drainage valves to be connected in parallel.

The motor 41 is placed in an actuator chamber 69. An O-ring gasket 70 placed around the pusher 66 serves to prevent any fluid leaking from the internal chamber 60 to the actuator chamber 69.

The gasket 70 could be replaced by a sealing bellows serving advantageously to limit friction on the pusher 66, and thus to limit power consumption.

In a variant, the pusher 66 may be replaced by a piezoelectric spring blade acting on the ball 65.

Holding the valve in an open or intermediate position then requires the piezoelectric spring blade to be powered permanently, whereas holding it in the closed position does not require any power, since the piezoelectric spring blade is then at rest.

The drainage valve 42 may be a passive valve, an on/off valve, or a progressive valve.

With a passive valve, the helical spring 67 constitutes resilient return means enabling the degree of opening to vary as a function of the pressure difference $P_d$.

With a progressive valve or an on/off valve, a helical spring 67 may also be present in order to act as resilient return safety means, remaining in a rest position that is employed in normal operation of the valve, but enabling the ball 65 to be separated from the valve seat 63 when the pressure difference $P_d$ reaches or exceeds the safe pressure $P_s$.

Figure 3:
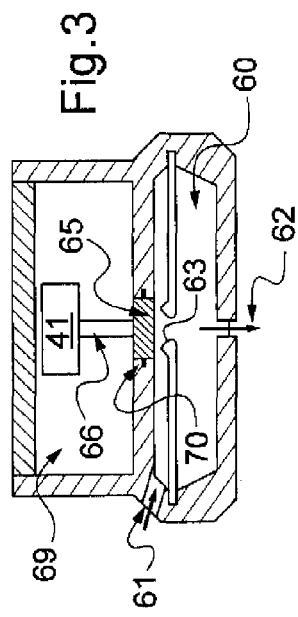

In FIG. 3, the valve member 65 is mechanically coupled to the motor 41 via the pusher 66, and the valve seat 63 is an elastomer diaphragm.

FIG. 4 shows another example of a drainage valve 42 suitable for use in a drainage device 10 according to exemplary embodiments of the invention.

The valve member 65 is constituted by an O-ring gasket fastened to the pusher 66 and capable of bearing against the valve seat 63.

FIG. 5 shows another example of a drainage valve 42 suitable for use in a device 10 according to exemplary embodiments of the invention.

The motor 41 acts on the pusher 66 that comes to bear against resilient return means in the form of a flat spring 80, which in turn bears against a valve member in the form of a ball 65.

In a variant, the flat spring 80 may be replaced by a helical spring.

Figure 8:
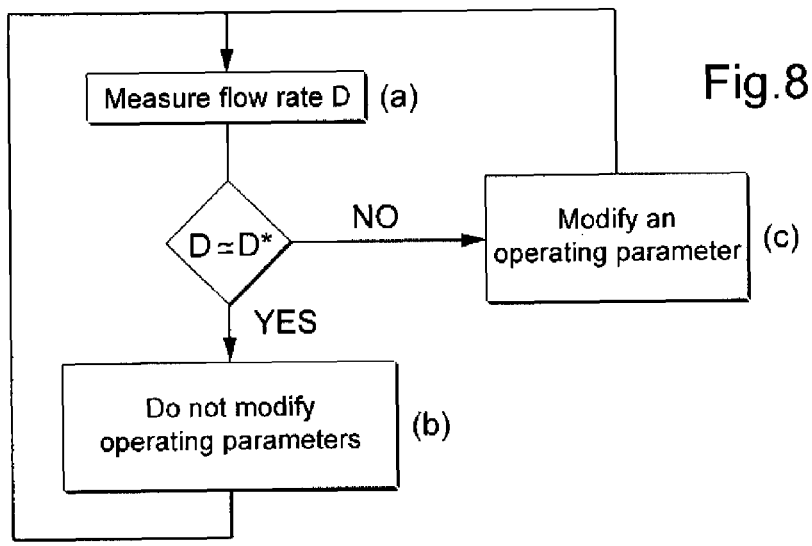
FIG. 8 shows a succession of steps that can be implemented when monitoring the measured value D of the flow rate in an embodiment using permanent drainage.

FIG. 8 shows a variant of FIG. 5 in which the motor 41 is suitable for imparting rotary drive to a cam-shaped pusher 66 suitable for compressing the flat spring 80.

The gasket 70 is constituted by an elastomer diaphragm.

FIGS. 7 and 8 relate to an embodiment using permanent drainage, in which cerebro-spinal fluid is drained continuously.

FIG. 7 is a graph plotting various measured values D of the flow rate as a function of time, the flow rate of the cerebro-spinal fluid being measured by the flowmeter, e.g. once every 10 seconds.

FIG. 8 shows the steps implemented after taking a measured value D of the flow rate of the cerebro-spinal fluid (step (a)).

If the measured flow rate D is substantially equal to the setpoint flow rate D* (step (b)), then no operating parameter is modified.

For example, the flow rates measured at (1) and (4) are substantially equal to the setpoint flow rate D* and do not give rise to any modification of an operating parameter (FIG. 7).

In contrast, if a significant difference is detected between the measured flow rate D and the setpoint flow rate D*, then the control unit determines a new value for one or more operating parameters so that the measured flow rate D tends towards the setpoint flow rate D* (step (c)).

By way of example, the flow rates measured at (2) and (3) give rise respectively to a decrease or to an increase in the extent to which the drainage valve is open (FIG. 7).

When the measured flow rate is greater than the limit flow rate $D_L$, as applies to the flow rate measured at (5), it is necessary to modify D*, in particular by triggering a calibration stage.

FIG. 9 relates to an embodiment using intermittent drainage and is in the form of a graph plotting various measured flow rate values D as a function of time.

The setpoint flow rate D is used to deduce both an opening frequency $F_0$ and a bolus volume $V_b$ corresponding to the volume of cerebro-spinal fluid that is to be evaluated during a drainage stage, such that;

$$D^* = F_0 \times V_b$$

During a drainage stage, the rate at which cerebro-spinal fluid is evaluated is measured by the flowmeter, once every 10 seconds. The volume V actually evaluated during this stage is determined by the control unit as a function of the measurement. When the volume V that has been evaluated is considered as being equal to the bolus volume $V_b$, then the valve is closed and the drainage stage is terminated.

Between drainage stages, the flow rate of the cerebro-spinal fluid through the valve is measured, e.g. 10 seconds after the end of the last drainage stage, and then once every 5 minutes, in order to detect any possible safety opening.

For example, in the graph of FIG. 9, a non-zero flow rate of the cerebro-spinal fluid is measured by the flowmeter at (7) between two drainage stages, which indicates that safety opening has occurred and requires D* to be modified, e.g. by triggering a calibration stage during which D* is increased, for example, as represented by the dashed line. When the measured flow rate D is zero, as applies to the flow rate measured at (8), then D* is not modified.

During a drainage stage, the measured value D of the flow rate may vary over a very wide range of values, as illustrated by the flow rates measured at (1), (2), (3), (4), (5), and (6).

When the flow rate value D moves outside the optimum accuracy range ($DP_{min}$ to $DP_{max}$) and/or the safe range ($DS_{min}$ to $DS_{max}$), as applies to the flow rates measured at (2) and at (4), the regulator of the control unit may act on one or more operating parameters in order to limit the amplitude of variations in the flow rate measured during drainage stages so as to bring the measured flow rate D towards an acceptable predetermined value, e.g. 75 mL/h, as applies to the flow rates measured at (3) and at (5). For example, it is possible to increase the opening frequency $F_0$ and/or the bolus duration $t_b$ (possibly as a function of the increase in bolus volume $V_b$).

Figure 10:
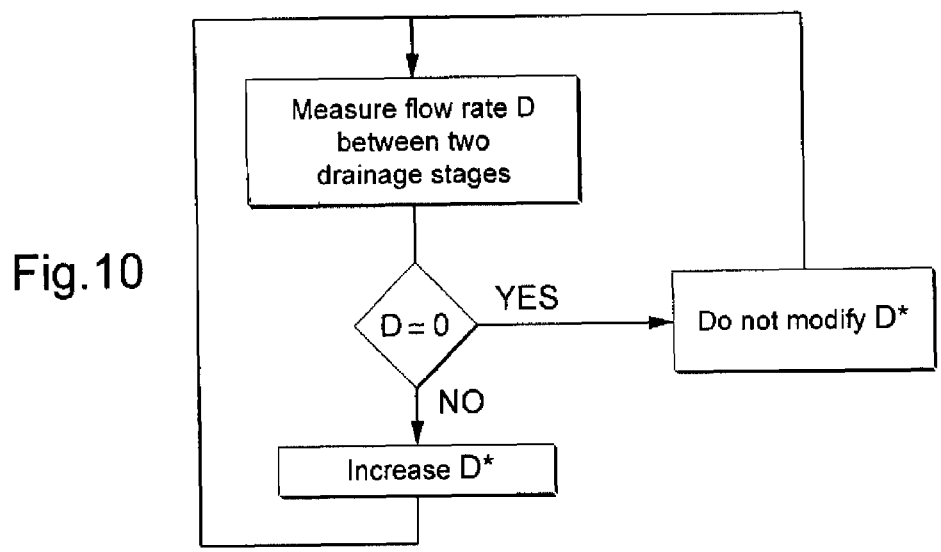
FIG. 10 shows a succession of steps that can be implemented during a calibration stage in an embodiment using intermittent drainage.
Figure 11:
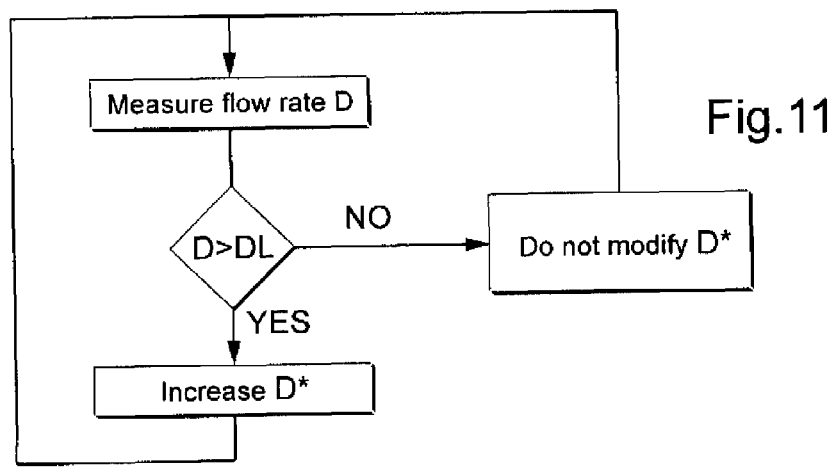
FIG. 11 shows a succession of steps that can be implemented during a calibration stage in an embodiment using permanent drainage.

FIGS. 10 and 11 show the steps implemented during a calibration stage, respectively for embodiments using intermittent and permanent modes of drainage.

By way of example, the calibration stage may be triggered on detecting a non-zero flow rate between two drainage stages (FIG. 10) or on detecting that a limiting flow rate $D_L$ has been exceeded (FIG. 11), e.g. corresponding to a critical value that should not be exceeded for the safety of the patient, e.g. in association with the safe pressure $P_s$.

During the calibration stage shown in FIG. 10, D* is modified, specifically increased, e.g. by 1 mL/h. The opening frequency $F_0$ and/or the bolus duration $t_b$ (possibly as a function of an increase in the bolus volume $V_b$) are modified accordingly. For example, $F_0$ may be increased, as shown in FIG. 9.

A plurality of successive calibration stages may be performed, e.g. so long as the flowmeter measures a non-zero flow rate of the cerebro-spinal fluid between two drainage stages, in accordance with the steps of FIG. 10.

During the calibration stage shown in FIG. 11, the setpoint flow rate D* is increased by a constant value, e.g. 1 mL/h.

By way of example, D* may be increased so long as the flowmeter measures a flow rate for the cerebro-spinal fluid that is greater than the limit flow rate $D_L$, in accordance with the steps of FIG. 11.

When the measured flow rate D is less than the limit flow rate $D_L$, then D* is no longer modified.

As can now be seen clearly, the invention provides a solution that is effective and reliable for draining cerebro-spinal fluid, this drainage being adaptable easily, and even automatically, to the patient and to the patient's living conditions.

Naturally, the present invention is not limited to the embodiments described and shown, which are given purely as non-limiting illustrative examples.

In particular, the various embodiments may be combined.

The invention claimed is:

1. An implantable drainage device for draining a patient's cerebro-spinal fluid, the device comprising:
   a drainage valve comprising a valve member and a valve seat;
   a control unit suitable for modifying an operating parameter of said valve, at least as a function of a measurement (D) of the fluid flow rate through said valve, said control unit being also suitable for re-evaluating a setpoint flow rate (D*) at regular intervals and/or following a particular event; and
   an actuator controlled by the control unit, suitable for modifying the operation of said valve as a function of said operating parameter as modified by the control unit;
   the device including a mass flowmeter suitable for taking said measurement of said flow rate of fluid through said valve.

2. A device according to claim 1, the mass flowmeter being a thermal flowmeter.

3. A device according to claim 1, the control unit including a regulator suitable for controlling the actuator so that the measured flow rate is servo-controlled on the setpoint flow rate (D*).

4. A device according to claim 1, the setpoint flow rate (D*) being re-evaluated every hour and/or immediately after the device is implanted in the patient's body and/or in the event of an abnormal flow rate being detected.

5. A device according to claim 1, the mass flowmeter taking measurements (D) of the flow rate in intermittent manner.

6. A device according to claim 1, the mass flowmeter taking measurements (D) of the flow rate solely during drainage stages.

7. A device according to claim 1, the control unit being suitable for modifying the operation of the valve when the flow rate measurement (D) moves out of an optimum accuracy range of the flowmeter and/or a safe range beyond which there exists a particular risk for the patient.

8. A device according to claim 3, the setpoint flow rate (D*) being settable, manually or by the control unit at regular intervals or following the detection of a need, to a value that is less than or equal to the value corresponding to the real production of cerebro-spinal fluid by the patient's body.

9. A device according to claim 1, the control unit being configured, during a cleaning stage, to cause the valve member to be spaced apart from the seat of the drainage valve by at least 0.5 mm.

10. A device according to claim 9, wherein the control unit causes a cleaning stage to be performed in the event of an abnormal flow rate being detected or at the request of a person, or at regular time intervals.

11. A device according to claim 9, wherein the control unit causes at least one cleaning stage to be performed per week.

12. A device according to claim 9, the duration of a cleaning stage being not less than 5 seconds.

13. A device according to claim 1, the control unit being configured in such a manner as to close the drainage valve completely in the event of the flowmeter detecting a reversal of the flow direction of cerebro-spinal fluid through the drainage valve.

14. A device according to claim 1, the drainage valve being a progressive valve or an on/off valve, and the actuator acting on the valve member of the drainage valve via resilient return safety means, the return force exerted by said resilient return safety means being determined so as to cause a safety opening to occur when the pressure difference ($P_d$) from upstream to downstream across the seat of the drainage valve exceeds a safe pressure ($P_s$).

15. A device according to claim 14, the safe pressure ($P_s$) being greater than or equal to 250 mm $H_2O$.

16. A device according to claim 1, the actuator comprising a motor suitable for holding the valve member in position without being powered.

17. A device according to claim 16, wherein the actuator is a motor of the piezoelectric type or the electrostatic type.

18. A device according to claim 1, including communication means implementing a radio frequency link and suitable for receiving and/or sending control instructions from or to the exterior of the patient's body.

19. A drainage system comprising:
   a device according to claim 1 and including communication means for communicating with the exterior of the patient's body; and
   a non-implantable control unit suitable for communicating with said communication means after said device has been implanted.

20. A method of controlling a valve of an implantable drainage device for draining the cerebro-spinal fluid of a patient, the device being the device according to claim 1, the method comprising:
   a regulation, the regulation being performed by means of a regulator controlling the actuator so that the measured flow rate is servo-controlled on the setpoint flow rate (D*), the setpoint flow rate (D*) being defined to a value that is less than the value needed for compensating exactly production of cerebro-spinal fluid by the patient.

* * * * *